United States Patent
Houser et al.

(10) Patent No.: US 6,217,585 B1
(45) Date of Patent: Apr. 17, 2001

(54) MECHANICAL STENT AND GRAFT DELIVERY SYSTEM

(75) Inventors: Russell A. Houser, Livermore; James G. Whayne, Saratoga; Sid D. Fleischman, Menlo Park, all of CA (US)

(73) Assignee: Converge Medical, Inc., Pleasanton, CA (US)

( * ) Notice: Subject to any disclaimer, the term of this patent is extended or adjusted under 35 U.S.C. 154(b) by 0 days.

(21) Appl. No.: 08/911,838

(22) Filed: Aug. 15, 1997

Related U.S. Application Data (60) Provisional application No. 60/024,079, filed on Aug. 16, 1996.

(51) Int. Cl.[7] .................................................. A61F 11/00
(52) U.S. Cl. ........................................ 606/108; 606/198
(58) Field of Search ...................................... 606/108, 198, 606/27, 113–115, 127–128, 200, 41; 604/105, 106, 107, 108

(56) References Cited

U.S. PATENT DOCUMENTS

| | | |
|---|---|---|
| 3,517,128 * | 6/1970 | Hines ..................................... 606/108 |
| 3,557,794 * | 1/1971 | Patten .................................... 128/345 |
| 4,214,587 | 7/1980 | Sakura, Jr. . |
| 4,366,819 | 1/1983 | Kaster . |
| 4,368,736 | 1/1983 | Kaster . |
| 4,607,637 | 8/1986 | Berggren et al. . |
| 4,624,257 | 11/1986 | Berggren et al. . |
| 4,657,019 | 4/1987 | Walsh et al. . |
| 4,787,386 | 11/1988 | Walsh et al. . |
| 4,917,087 | 4/1990 | Walsh et al. . |
| 4,917,090 | 4/1990 | Berggren et al. . |
| 4,917,091 | 4/1990 | Berggren et al. . |
| 5,156,610 * | 10/1992 | Geger ..................................... 606/159 |
| 5,156,613 | 10/1992 | Sawyer . |
| 5,234,447 | 8/1993 | Kaster et al. . |
| 5,275,610 * | 1/1994 | Eberbach .............................. 606/198 |

(List continued on next page.)

FOREIGN PATENT DOCUMENTS

| | | |
|---|---|---|
| WO 96/22745 | 8/1996 | (WO) . |
| WO 97/43961 | 11/1997 | (WO) . |
| WO 98/03118 | 1/1998 | (WO) . |
| WO 98/07399 | 2/1998 | (WO) . |

OTHER PUBLICATIONS

Cragg et al. (1982). "Endovascular Diathermic Vessel Occlusion," *Radiology.* 144:303–308.

Gorisch et al. (1982). "Heat–Induced Contraction of Blood Vessels," *Lasers in Surgery and Medicine.* 2: 1–13.

Heijmen et al. (1999). "A Novel One–Shot Anastomotic Stapler Prototype for Coronary Bypass Grafting on the Beating Heart: Feasibility in the Pig," *J. Thorac Cardiovasc Surg.* 117: 117–125.

*Primary Examiner*—Michael Buiz
*Assistant Examiner*—Lien Ngo
(74) *Attorney, Agent, or Firm*—Morrison & Foerster LLP (57) ABSTRACT

A deployment device for stents and grafts includes a catheter, an expansion framework or cage near the catheter distal end, and a means for controlling expansion from a proximal end of the catheter. The cage is formed of a plurality of elongate strands coupled at opposite ends to the catheter and to the control device. Axial movement of the control device relative to the catheter either elongates the strands to radially collapse the cage, or axially reduces the distance between the strand ends for radial enlargement. In one embodiment the control device is a stylet contained in a lumen of the catheter and extending beyond the catheter distal end. The strands are fixed at their opposite ends to the catheter distal end and the stylet distal end. In another embodiment, the strands are coupled to proximal and distal rings along the catheter, with one of the rings being axially movable by a wire to radially expand and reduce the cage.

20 Claims, 10 Drawing Sheets

U.S. PATENT DOCUMENTS

| | | | |
|---|---|---|---|
| 5,354,309 | 10/1994 | Schnepp-Pesch et al. | 606/198 |
| 5,354,310 * | 10/1994 | Garnic et al. | 606/198 |
| 5,405,322 | 4/1995 | Lennox et al. . | |
| 5,409,460 | 4/1995 | Krumme | 604/107 |
| 5,433,723 | 7/1995 | Lindenberg | 606/198 |
| 5,443,497 | 8/1995 | Venbrux . | |
| 5,503,635 | 4/1996 | Sauer et al. . | |
| 5,540,679 * | 7/1996 | Fram et al. | 606/27 |
| 5,540,713 | 7/1996 | Schnepp-Pesch et al. | 606/198 |
| 5,598,848 * | 2/1997 | Swanson et al. | 128/696 |
| 5,618,301 | 4/1997 | Hauenstein et al. | 606/198 |
| 5,665,117 | 9/1997 | Rhodes . | |
| 5,669,934 | 9/1997 | Sawyer . | |
| 5,690,675 | 11/1997 | Sawyer et al. . | |
| 5,696,504 | 12/1997 | Gifford, III et al. . | |
| 5,713,907 * | 2/1998 | Hogendijk et al. | 606/108 |
| 5,716,393 | 2/1998 | Lindenberg et al. | 623/1 |
| 5,749,895 | 5/1998 | Sawyer et al. . | |
| 5,755,775 | 5/1998 | Trerotola et al. . | |
| 5,779,718 | 7/1998 | Green et al. . | |
| 5,824,015 | 10/1998 | Sawyer . | |
| 5,860,974 * | 1/1999 | Abele | 606/41 |
| 5,868,759 | 2/1999 | Peyser et al. . | |
| 5,868,761 | 2/1999 | Nicholas et al. . | |
| 5,931,842 | 8/1999 | Goldsteen et al. . | |
| 5,934,286 | 8/1999 | Maginot . | |
| 5,938,672 | 8/1999 | Nash . | |
| 5,938,696 | 8/1999 | Goicoechea et al. . | |
| 5,944,019 | 8/1999 | Knudson et al. . | |
| 5,944,730 | 8/1999 | Nobles et al. . | |
| 5,944,738 | 8/1999 | Amplatz et al. . | |
| 5,944,750 | 8/1999 | Tanner et al. . | |
| 5,954,764 | 9/1999 | Parodi . | |
| 5,957,940 | 9/1999 | Tanner et al. . | |
| 5,968,068 | 10/1999 | Dehdashtian et al. . | |
| 5,968,089 | 10/1999 | Krajiček . | |
| 5,972,017 | 10/1999 | Berg et al. . | |
| 5,976,153 | 11/1999 | Fischell et al. . | |
| 5,976,178 | 11/1999 | Goldsteen et al. . | |
| 5,976,179 | 11/1999 | Inoue . | |

\* cited by examiner

MECHANICAL STENT AND GRAFT DELIVERY SYSTEM

This application claims the benefit of Provisional Application No. 60/024,079 entitled "Mechanical Stent and Graft Delivery System", filed Aug. 16, 1996.

BACKGROUND OF THE INVENTION

The present invention relates to systems for percutaneously delivering and deploying vascular stents and grafts, and more particularly to devices for positioning a stent or graft within a target vessel, then radially expanding the stent or graft into intimate contact with vessel tissue.

Stenosed vessels traditionally have been opened by angioplasty, with a balloon placed into the stenosed vessel and expanded radially to open the vessel. A frequently recurring problem with angioplasty is the eventual restenosis of the vessel. One approach to counteract restenosis involves positioning radially expandable stents within treated vessels. Typically, balloons are used to open the vessel wall and to expand the stent. However, size and burst pressure considerations limit the efficacy of balloons in expanding the stent. Multiple balloons typically are used to expand a single stent, due to the tendency of balloons to burst during stent expansion.

Another vessel condition requiring treatment, the aneurysm, results from weak blood vessel walls which can balloon due to the intrinsic pressure in the vessel. Aneurysms can apply pressure on adjacent anatomic structures, producing abnormal function. In addition, vessels have a potential to rupture, causing internal bleeding and potentially life threatening conditions. Grafts are used to isolate aneurysms or other blood vessel abnormalities from the blood pool, reducing pressure on the weakened vessel wall. Grafts reduce blood loss in the event of vessel rupture. Currently, grafts are expanded into place using balloon catheters. Some large diameter vessels, e.g. the aorta, require large diameter balloons to fully expand the graft into place. At the same time, the balloon must be collapsible into a low delivery profile during introduction and withdrawal, a factor that limits balloon diameters and wall thicknesses.

Frequently, calcified lesions result in weakened blood vessel wall sections, where a stent or graft must be radially expanded at a gradual rate to minimize the risk of further injury to the vessel. However, the paramount concern of maintaining blood flow through the vessel necessitates either providing a profusion lumen, or periodic evacuations of the balloon to allow blood flow, thus prolonging the radial expansion procedure.

Thus, a need exists for a mechanical delivery system which, in the non-linear environment found within blood vessels, is capable of expanding into an enlarged, predetermined configuration to cause an accompanying stent or graft to fully expand. The delivery system must facilitate introduction of a stent or graft into the target vessel, permit enlargement of the stent or graft within small vessels, and facilitate continuous profusion of blood around the expanding device during the procedure. The system also must be capable of exerting large radial forces to expand stents or grafts having excessive stiffness, or more generally to expand any grafts or stents within excessively stenosed vessels.

Particularly, there is a need for a delivery system which can expand stents or grafts without the need of an inflation medium. The delivery system must be capable of targeting large vessels such as the aorta, or small vessels such as the arteries or arterioles. Although the delivery system and particularly its stent or graft expansion region can be scaled to different sizes, preferably a single device or system is usable over a wide range of vessel and prosthesis sizes.

SUMMARY OF THE INVENTION

To address the above and other objects, there is provided an apparatus for deploying expandable prostheses within body lumens. The apparatus includes an elongate and flexible catheter having a proximal end and a distal end. The catheter is body insertable to position the distal end within a body lumen, with the proximal end remaining outside the body. A control device is disposed along the catheter. The apparatus further includes an expansion framework comprising a plurality of elongate compliant strands. The strands are coupled at a first location that is axially fixed with respect to the catheter, and further are coupled at a second location that is axially fixed with respect to the control device. The elongate strands cooperate to determine a profile of the expansion framework. The control device is operable from the proximal end to increase an axial distance between the first and second locations to reduce the framework to a reduced-radius state for intravascular delivery of an unexpanded tubular prosthesis in surrounding relation to the framework. Alternatively, the control device is operable to reduce the axial distance to radially expand the framework, thereby to radially expand an expandable prosthesis surrounding the framework.

The apparatus or system enables a physician to accurately position a stent or graft within a target vessel of a patient, and to expand the stent or graft without the need for an inflation medium. The system permits percutaneous access, requiring a smaller puncture site than a surgical cut-down. The delivery system expands the stent or graft after accurate positioning.

According to one aspect of the invention, the apparatus is composed of a number of strands bound proximally to the catheter, and distally to a stylet that functions as the control device. The stylet runs the length of the catheter body, disposed within a lumen of the catheter. When retracted, the stylet causes the strands to exert a radial force for expanding a stent or graft. When advanced distally, the stylet moves the strands into their reduced-radius state, in which they extend axially, parallel to and adjacent the stylet. The aspect ratio of the maximum expanded radius to the minimum or collapsed radius depends on movement of the stylet. The expansion of the wire strands may be regulated by stylet motion.

If desired, an elastomeric sleeve can surround the strands at least over medial regions of the strands. As the stylet is retracted, the strands are increasingly curved and extend increasingly radially outward, causing the elastomeric covering or sleeve to radially expand. The elastomeric covering may incorporate slits to permit sustained perfusion through the vessel, thus to enable prolonged expansion of the delivery system without compromising cardiac output through the vessel.

According to one desired enhancement, the strands are preformed to exert a radially outward force throughout a larger region of the stent or graft. The stiffness of the strands can be controllably varied over their respective lengths, to produce a more uniform expansion profile. This can involve varying the thickness or the width of the strands, or both.

According to another embodiment, the strands are electrically conductive and connected to a radio frequency (RF) signal generator. RF energy is applied to one or more of the strands, causing ohmic or resistive heating near the graft or stent. This is believed to help secure the graft to the vessel, and also may promote quicker formation of an endothelial layer over the prosthesis. As an alternative, a DC power source can be coupled to opposite ends of the strands for resistive heating.

According to a further embodiment, the strands may support balloon chambers which are porous or microporous to permit their use to deliver a drug to the target vessel. Perfusion is maintained between the balloon chambers to permit longer inflation durations for diffusing the maximum amount of the desired drug to the target vessel wall.

IN THE DRAWINGS

For a further understanding of the above and other features and advantages, reference is made to the following detailed description and to the drawings, in which.

DETAILED DESCRIPTION OF THE PREFERRED EMBODIMENTS

Figure 1:
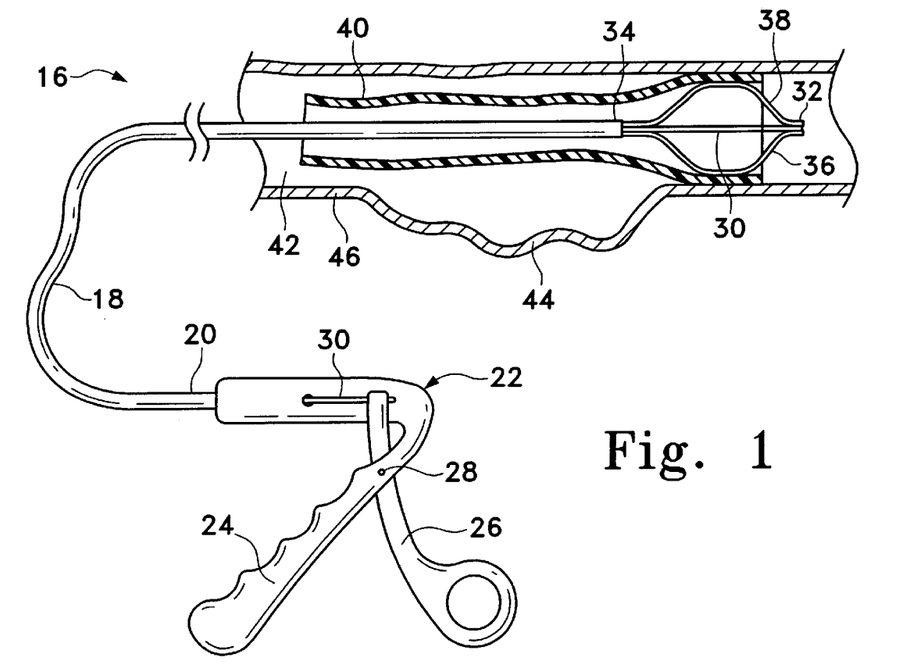
FIG. 1 is a schematic view of an expansion system used to deploy a graft within a vessel according to the present invention.

Turning now to the drawings, there is shown in FIG. 1 a system 16 for expanding a stent or graft within a body lumen. The system includes an elongate, flexible catheter 18. At the proximal end 20 of the catheter is a handle assembly 22, with handle sections 24 and 26 mounted to one another pivotally at 28. The proximal end of the catheter is attached to handle section 24. A stylet 30, contained within a catheter lumen and running the length of the catheter, extends proximally to a point of attachment with handle section 26, so that the stylet moves axially relative to the catheter as handle section 26 is pivoted relative to handle section 24.

Stylet 30 extends distally beyond catheter 18, to a distal tip 32 spaced apart from a distal tip 34 of the catheter. A plurality of flexible strands 36 are integrally fixed to distal tip 32 of the stylet, and thus are movable axially relative to the catheter with the stylet. Strands 36 are equal in length, and uniformly circumferentially arranged about stylet 30, i.e. about a longitudinal axis of the catheter and stylet, which can be considered substantially centered within the catheter although it need not be precisely centered.

The strands cooperate to provide an expansion framework or cage 38. The cage profile, most usefully the radius, varies with the axial distance between the locations of strand attachment, i.e. between catheter distal tip 34 and strand distal tip 32. Thus, by properly pivoting handle section 26 at the proximal end of the device, cage 38 can be controlled in its profile from a reduced-radius delivery state corresponding to a maximum axial separation between distal tips 32 and 34, to an enlarged-radius configuration as shown. In the delivery state, the strands are adjacent and substantially parallel to the stylet. In the enlarged-radius state, adjacent strands are circumferentially spaced apart from one another, and curved as shown. The strands are sufficiently compliant to change the radius in response to changes in the axial distance, but also sufficiently stiff to expand a prosthesis radially outward against tissue.

FIG. 1 shows the use of system 16 to deploy a graft 40 within a target vessel 42, to shunt an aneurysm 44 within the vessel. With handle sections 24 and 26 somewhat separated from one another as shown, stylet 30 is partially retracted to expand cage 38 against graft 40, thus also radially expanding the graft into contact with a tissue wall 46 of the vessel. Moving the handle sections closer together, i.e. rotating handle section 26 clockwise as viewed in the figure further retracts the stylet and further enlarges the cage. Conversely, counterclockwise rotation of handle section 26 moves stylet 30 distally relative to the catheter, increasing the axial separation of tips 32 and 34 to collapse the cage.

Graft 40 is of the type that requires an external force for expansion, conventionally applied through an inflatable balloon. Thus, when cage 38 is radially contracted, the distal end of the graft remains expanded. The contracted cage can be moved proximally, to radially expand the unexpanded segments of the graft.

The spring force or restoring force within strands 36 tends to straighten the strands axially and extend the stylet, thus to collapse cage 38 when the handle is released. If desired, the handle can be spring loaded to supply a restoring force that cooperates with the strand restoring force. Then, retracting the stylet to expand the cage is accompanied by the tactile sense of squeezing the handle, so that the operator associates increased pressure on the handle with increased balloon expansion. Further if desired, a pressure gauge can be mounted on the handle to measure the pressure on stylet 30, which correlates to the pressure exerted on the graft or stent, taking into account the friction on the stylet within the catheter body. This configuration promotes expanding and collapsing the handle to sequentially expand multiple sections of the graft or stent.

Figure 2:
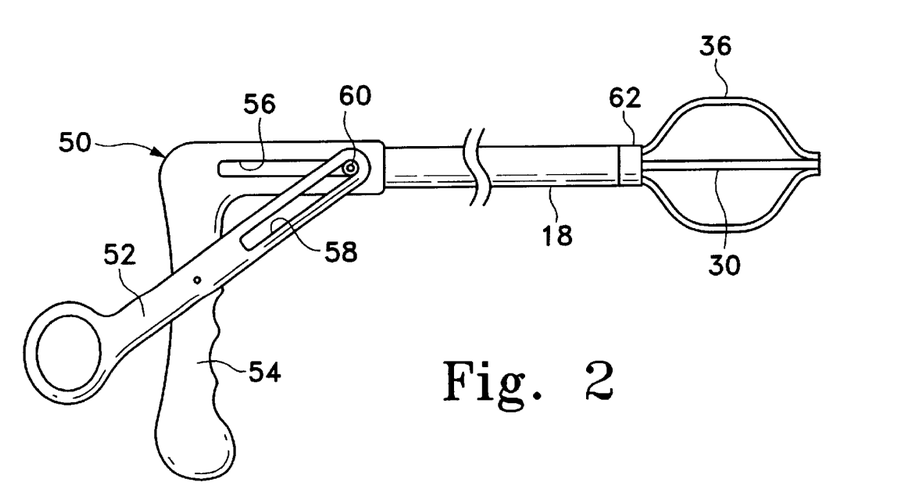
FIG. 2 is an elevation of the system of FIG. 1 with a modified handle.

In FIG. 2, system 16 is shown with a slightly modified handle 50 including a handle section 52 pivotally mounted to a handle section 54 that receives proximal end 20 of the catheter. An axial slot 56 is formed in handle section 54, and an elongate slot 58 is formed in handle section 52. A slide 60, attached to the proximal end of stylet 30, slides within slots 56 and 58. Thus, as the handle sections are drawn together by rotating handle section 52 counterclockwise, slide 60 moves proximally within slot 56 to retract the stylet.

As seen in FIG. 2, an annular anchor 62 secures the proximal ends of strands 36 to the catheter distal tip. Anchor 62 can form an interference fit, a shrink fit, be it a spot weld or solder junction. Alternatively, the strand proximal ends can be secured with adhesives. The strand proximal ends lie adjacent the outside wall of the catheter when surrounded by the shrink tubing, and when secured with adhesives may be disposed along the catheter interior wall as well.

Figure 3:
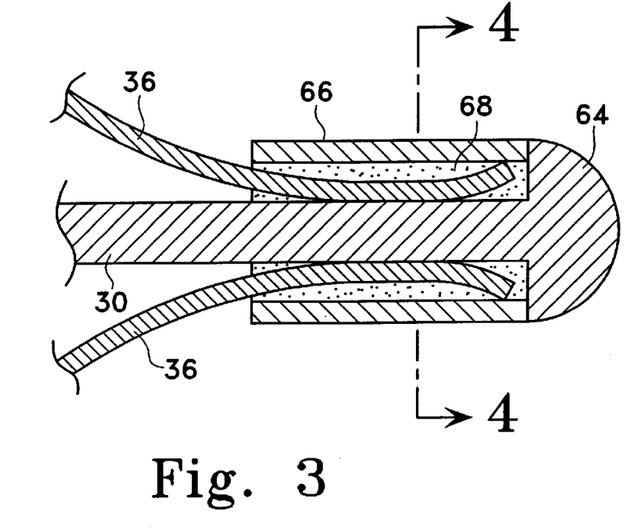
FIG. 3 illustrates in more detail a coupling of the strands and a control stylet.
Figure 4:
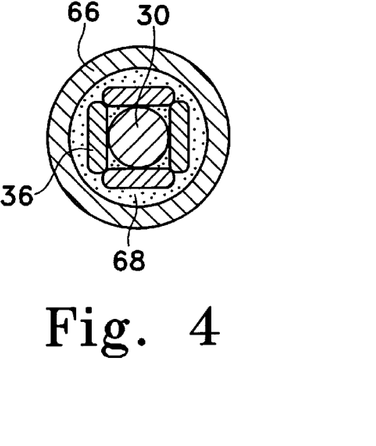
FIG. 4 is a cross-section taken along the line 4—4 in FIG. 3.

The distal ends of the strands are integrally fixed to the stylet distal tip. As seen in FIGS. 3 and 4, stylet 30 includes an enlarged head portion 64. Adjacent the head is a clamping tube 66 surrounding and securing the strand distal ends. An adhesive can be provided to further secure the strand ends, as indicated at 68. With the transverse profiles of the strands shaped as shown in FIG. 4, the adhesive advantageously occupies the space between the strands and clamping tube 66.

Figure 5A:
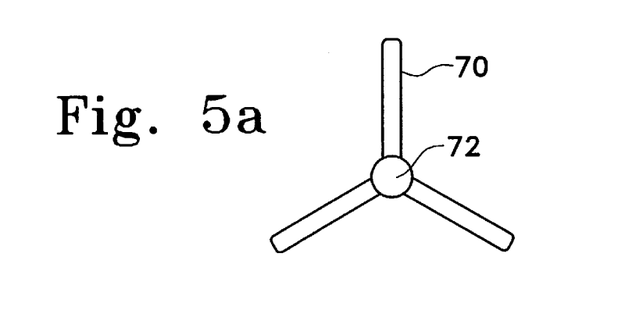
FIGS. 5a and 5b illustrate two different alternative cages or expansion frameworks employed in the system.
Figure 5B:
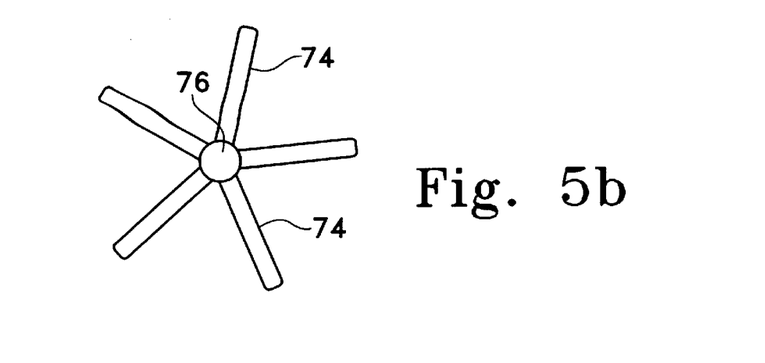

As seen in FIG. 4, four strands are employed, uniformly circumferentially arranged about stylet 30, i.e. with adjacent strands angularly spaced apart 90 degrees. Other strand configurations are suitable, for example three strands 70 arranged around a stylet 72 at 120 degree intervals as in FIG. 5a, and five strands 74 arranged about the stylet 76 in 72 degree intervals as in FIG. 5b. The preferred number of strands is three to six. Normally the strands are of equal length, equal size (transverse profile), and are distributed uniformly about the stylet to exert balanced outward pressure in different radial directions. However, to accommodate non-linear vessel walls or to deliver non-uniform pressure radially or axially, strand lengths can vary, be preshaped into different configurations, and have differing stiffness profiles.

Figure 6A:
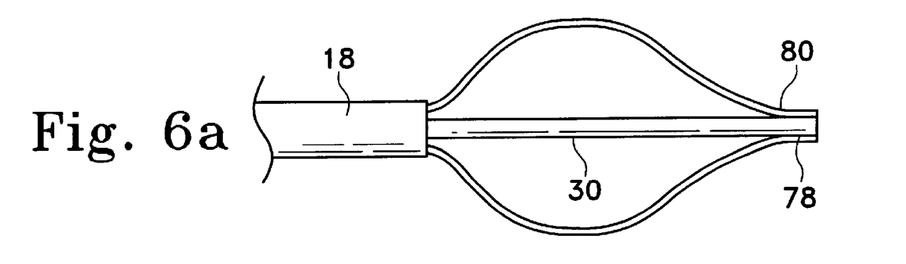
FIGS. 6a–c illustrate different distal couplings of framework strands.
Figure 6B:
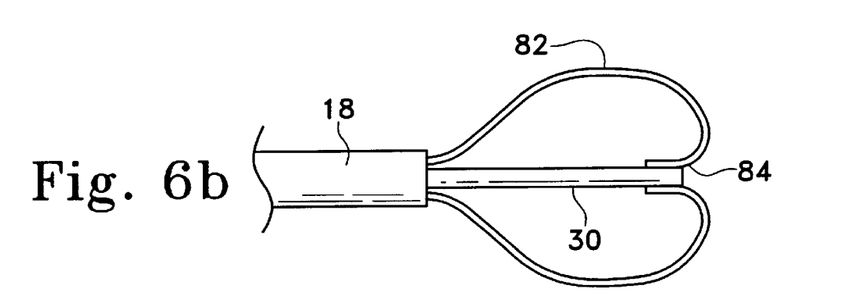
Figure 6C:
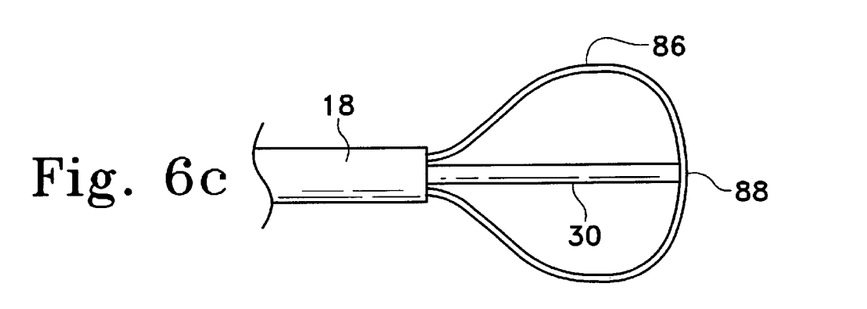

FIGS. 6a, 6b and 6c show alternative couplings of the strands to the stylet distal end. In FIG. 6a, an adhesive 78 secures strand distal ends 80 parallel to the stylet. In FIG. 6b, strands 82 are formed into reverse loops so that distal ends 84 are parallel to the stylet but proximally rather than distally directed for an inverted mounting. In FIG. 6c, a strand 86 is formed into a loop with a midpoint 88 of the loop secured to the stylet distal tip, so that strand 86 replaces two oppositely positioned strands of the other embodiments.

Figure 7A:
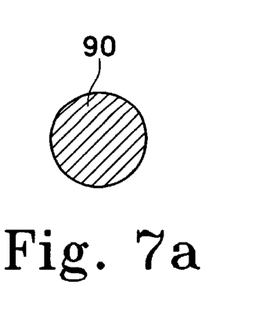
FIGS. 7a–c illustrate different strand structures.
Figure 7B:
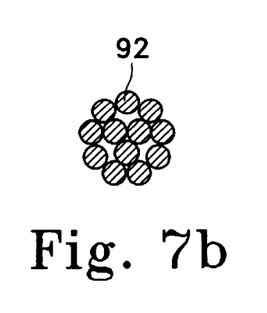
Figure 7C:
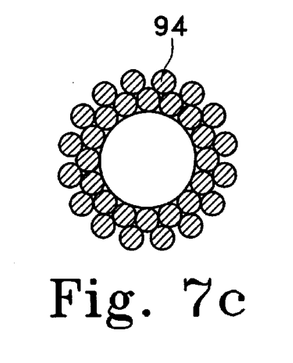

As shown in FIGS. 7a–c, the strands can take a variety of forms, for example a single wire or filament 90 as in FIG. 7a, a set of smaller wires or filaments packed together in the form of a cable 92 as in FIG. 7b, or with multiple filaments combined to provide a tubular strand 94 as in FIG. 7c. The stylet also can be manufactured from a hypotube, guidewire or solid wire and may be formed for example of stainless steel 17-7, stainless 304, another metal or metal alloy, or a thermoplastic polymer or composite material.

Figure 8:
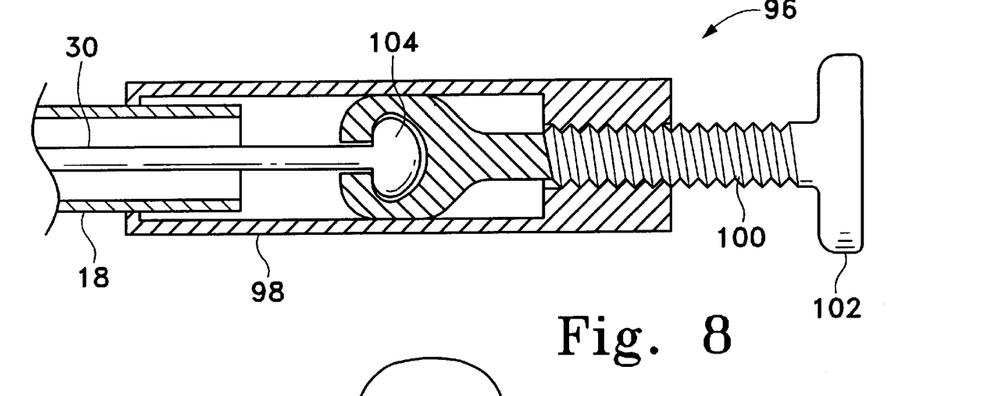
FIG. 8 illustrates an alternative embodiment proximal stylet control.

FIG. 8 shows an alternative embodiment stylet control handle assembly 96 that can be used in system 16 in lieu of handle 22 or handle 50. Handle assembly 96 includes a cylindrical body 98 that integrally receives proximal end 20 of catheter 18. A rotatable member 100 is threadedly engaged within body 98, and has a knob 102 at its proximal end to facilitate rotation by hand. At its distal end, member 100 includes an opening to receive an enlarged proximal end 104 of stylet 30, in a manner that allows rotation of the handle without rotating the stylet. Thus, knob 102 is rotatable either to extend or retract the stylet. In this configuration, the distance between a proximal end of body 98 and knob 102 correlates to the degree of cage radial expansion. As an alternative, the stylet can be directly attached to the knob, but the connection shown avoids any torquing of the stylet due to knob rotation.

Figure 9:
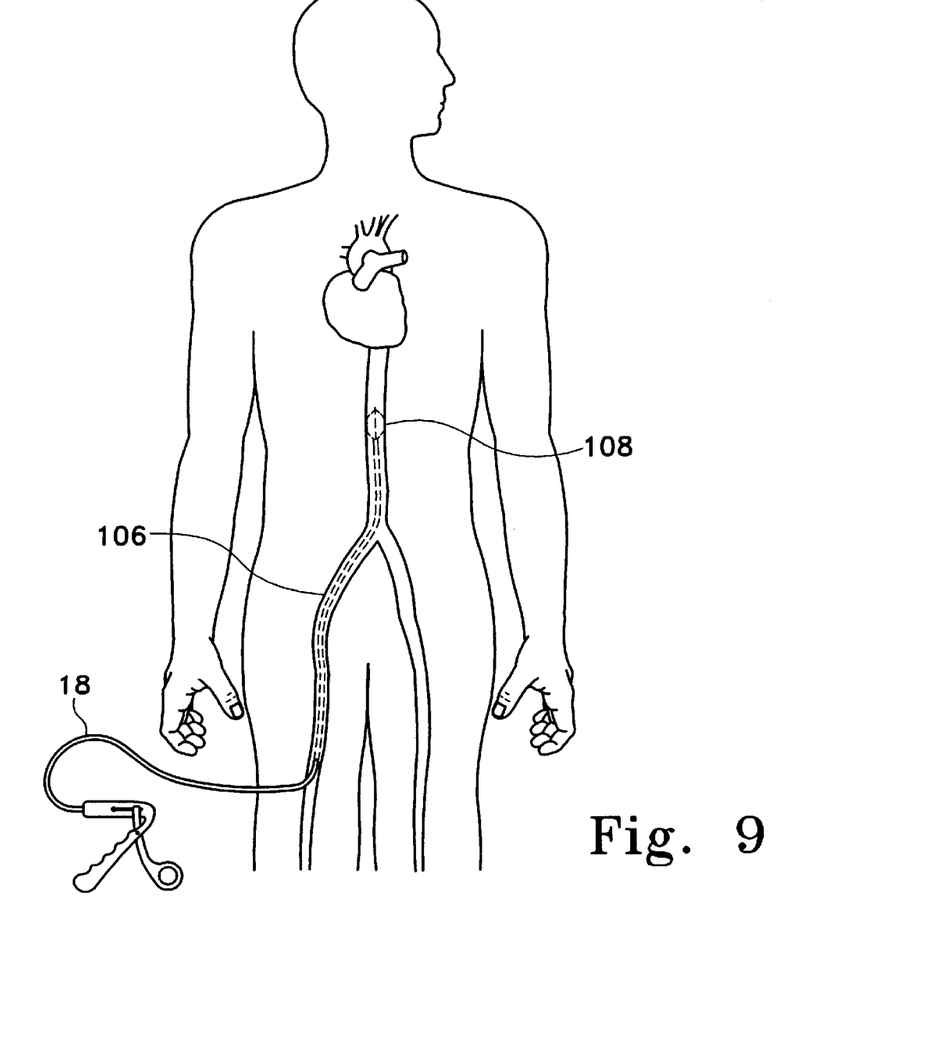
FIG. 9 schematically illustrates use of the system to deploy a prosthesis.

System 16 is used to deploy a prosthesis (e.g. a stent or graft) transvenously to an intended treatment site after percutaneous entry. For example, as seen in FIG. 9, catheter 18 is inserted by its distal end into a femoral artery 106, then advanced upwardly, usually over a previously inserted guide catheter, until a prosthesis carried by catheter 18 near its distal end is positioned at the intended treatment site, indicated at 108. Then, the handle is manipulated to radially expand the prosthesis into an intimate contact against vessel wall tissue, thus to anchor the prosthesis. Normally the unexpanded tubular prosthesis is held in frictional engagement in surrounding relation to cage 38 and catheter distal tip 34. If desired, angular slots, angular ridges or other prosthesis retaining features can be formed into the catheter along its exterior wall, to further ensure a secure mounting of the prosthesis as it is carried transluminally on the catheter.

Figure 10:
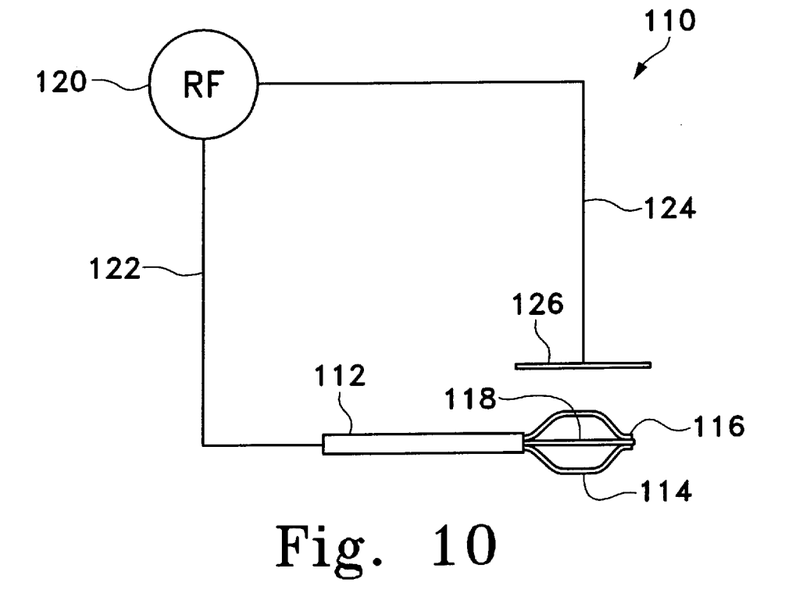
FIGS. 10 and 11 illustrates an alternative embodiment system in which an RF current is provided to the framework.
Figure 11:
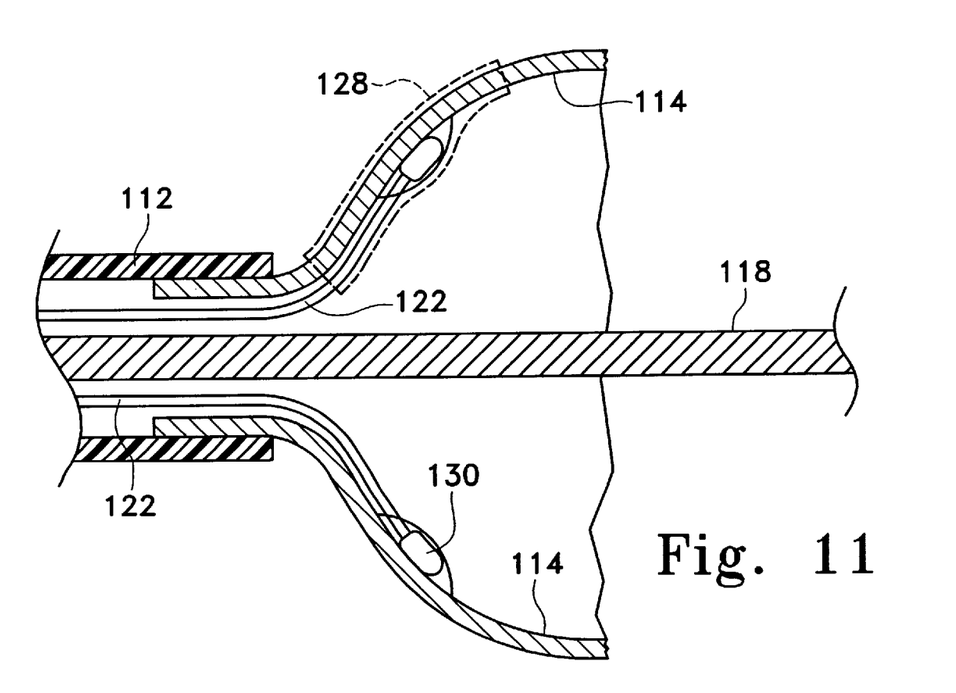

FIGS. 10 and 11 disclose another embodiment device 110 including a catheter 112, a plurality of strands 114 coupled to the distal end 116 of the catheter, and to the distal tip of a stylet 118, as with previous embodiments. Strands 114 are electrically conductive, and are electrically coupled to an RF generator 120 through a conductive line 122. Another line 124 connects the RF generator to an indifferent electrode 126, of the type that typically remains outside of the body and is placed in near proximity to an internal electrode. In this case, strands 114, or one or more of the strands, cooperate to provide the internal electrode. When generator 120 is activated to supply an RF current to the strands, a current is generated between the strands and indifferent electrode 126, ohmically heating the strands and the surrounding tissue.

As seen in greater detail in FIG. 11, a plurality of lines or signal wires 122 can be coupled through spot welding, soldering, or laser welding to the conductive strands. The bond between the signal wires and strands also may be secured or augmented with adhesives, to increase bond strength. If desired, strands 114 may be selectively masked with insulators as indicated at 128, to more selectively deliver RF energy. Also, as indicated at 130, a junction between a strand 114 and a signal wire 122 can form a thermocouple if different metals are used for these respective components. The induced voltage, when calibrated with respect to a temperature response, can be used to regulate the provision of RF energy to the vessel wall.

As an alternative, a DC power source can be coupled to opposite ends of the strands through two electrically isolated lines, whereby strands 114 experience resistance heating and then heat surrounding tissue.

In either event, heating is believed to enhance the bonding of the stent or graft to the vessel wall. Heating also is likely to promote the formation of an endothelial layer over the stent or graft and subsequent healing of the vessel wall. A more secure graft or stent is better able to remain in place within the vessel, avoiding axial movement. Further, there is less likelihood of leaks that prevent or hinder healing of the damaged vessel. Reducing the required pressure applied to the vessel may avoid rupturing of the aneurysm. Finally, heating of the vessel wall may increase the kinetics of drug diffusion into the expanded vessel, which may reduce or prevent restenosis.

As an alternative to heating the strands themselves, a heating implement may be placed proximate the cage, either proximal or distal thereto. For example, the heating mechanism can be a coiled wire or a coated metallic section. DC or RF energy can be applied to the metallic section to resistively heat the blood vessel or prosthesis. Heating a stent or graft would increase the rate at which the stent transforms states and expands in the vessel, in the event that the stent or graft is constructed of a memory elastic material which transforms from an austenite to a martensite material at temperatures at or above body temperature.

Figure 12:
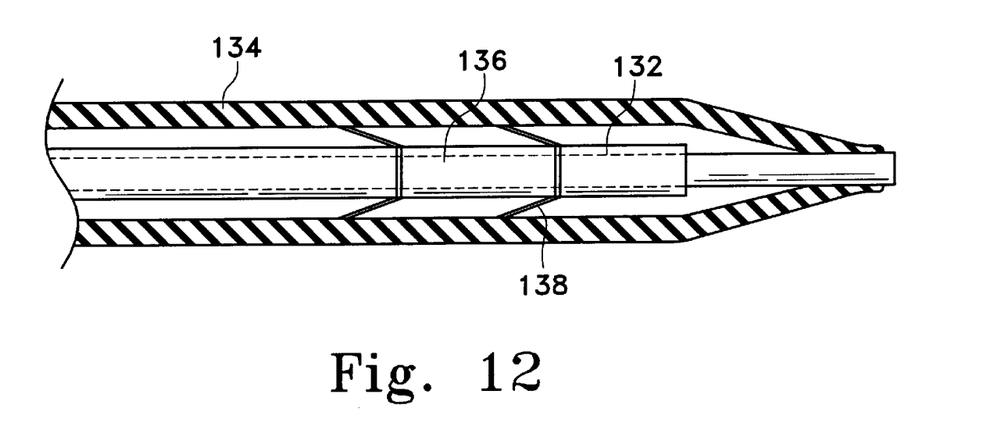
FIGS. 12 and 13 illustrate another alternative embodiment system employing a movable shaft for radial expansion.
Figure 13:
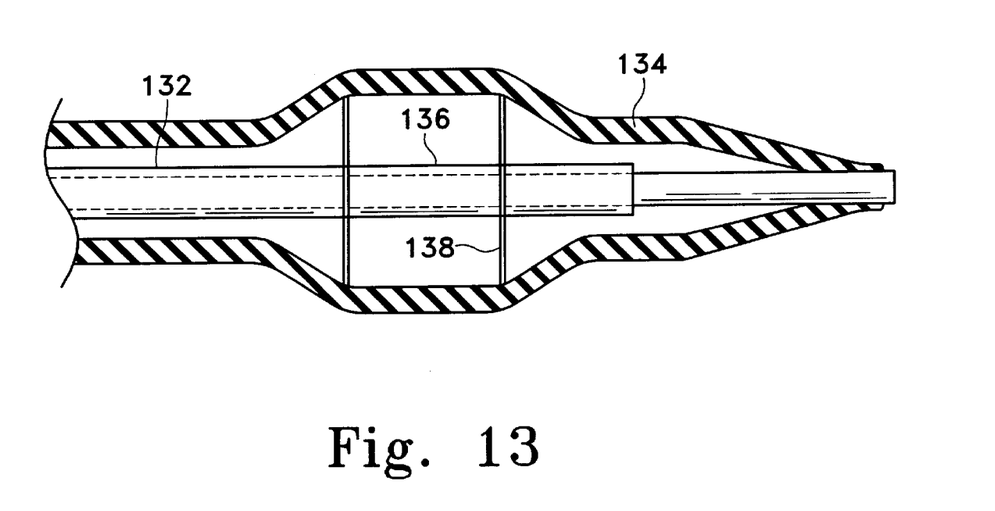

FIGS. 12 and 13 show the distal end region of an alternative embodiment device in which a catheter shaft 132 is surrounded by an expandable tubular wall 134 constructed of an elastomer, such as silicone rubber or urethane. In the absence of an external force, tubular wall 134 is in a collapsed configuration surrounding and adjacent the catheter shaft. A sleeve 136 surrounds the catheter shaft. Expansion leaves or strands 138 extend from the proximal and distal ends of the sleeve to the expandable wall. The strands may be bonded to the elastomer thermally, thereby embedding the wire of the expansion leaves into the expandable tubing wall. Alternatively, the strands may be bonded to the expandable wall with adhesives. The strands may be bonded to catheter shaft 132 through spot welding, soldering, or through holes drilled through the shaft body. Adhesives also may be employed, which enables the strands on each side of the shaft to be formed from a single wire.

Expandable tubular wall 134 may be bonded at its proximal and distal ends to the catheter either thermally or mechanically, e.g. with shrink tubing or adhesives. The expandable tubing wall can be made of an intrinsically porous material, or formed with pores of a desired size through laser drilling or other techniques for drug delivery if desired. The tubings may be thermoplastic polymers. The elastomer may incorporate slits through which blood may continuously flow during expansion of the elastomer, to enable prolonged deployment of the delivery system without compromising hemodynamics. This is especially important when expanding grafts in the aorta or expanding stents in the coronary arteries.

When the expandable wall is completely collapsed, strands 138 are substantially parallel to shaft 132. Partial expansion is shown in FIG. 12, where the strands form an acute angle with the shaft. Full expansion, shown in FIG. 13, is achieved when the strands are substantially perpendicular to the shaft. The aspect ratio of the expanded wall to the collapsed wall profile depends on the lengths of the strands, the length of the expansion area of the expandable wall, and the percent elongation the elastomer can withstand. Elastomers typically can elongate to between three and ten times their unexpanded length before failure. The available diameter for expansion may be increased by increasing the length of the expansion area. As the number of expansion strands is increased, the expansion profile becomes more uniform radially. The expansion strands and/or the elastomer may be radiopaque to facilitate visualization under fluoroscopy.

Figure 14:
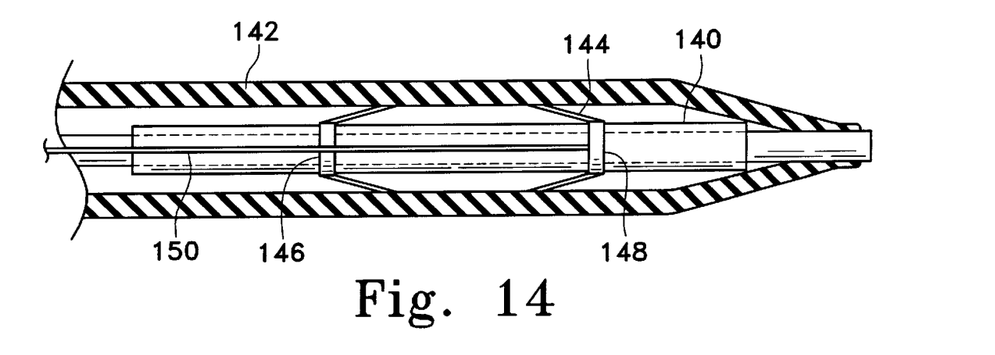
FIGS. 14 and 15 illustrate another alternative embodiment employing a wire in tension to control radial expansion.
Figure 15:
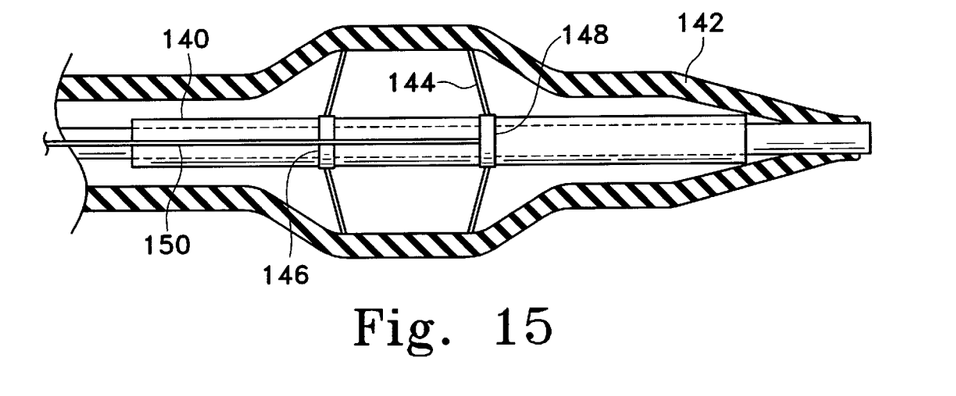

FIGS. 14 and 15 show the distal end of a device incorporating a catheter shaft 140 surrounded by an expandable tubing wall 142. A plurality of strands 144 are arranged circumferentially about shaft 140, attached to tubing wall 142 over an expansion portion thereof. The strands further are attached to catheter shaft 140, at a proximal ring 146 and at a distal ring 148. The proximal ring is secured integrally on the shaft, while the distal ring is mounted slidably on the shaft. A pull wire 150 is attached to the distal ring.

Radial expansion of tubing wall 142 is achieved by pulling wire 150 proximally, i.e. to the left as viewed in FIGS. 14 and 15. This shortens the axial distance between rings 146 and 148, which increases the angle between the strands and the shaft to expand the outer tubing radially, as seen in FIG. 15.

Figure 16:
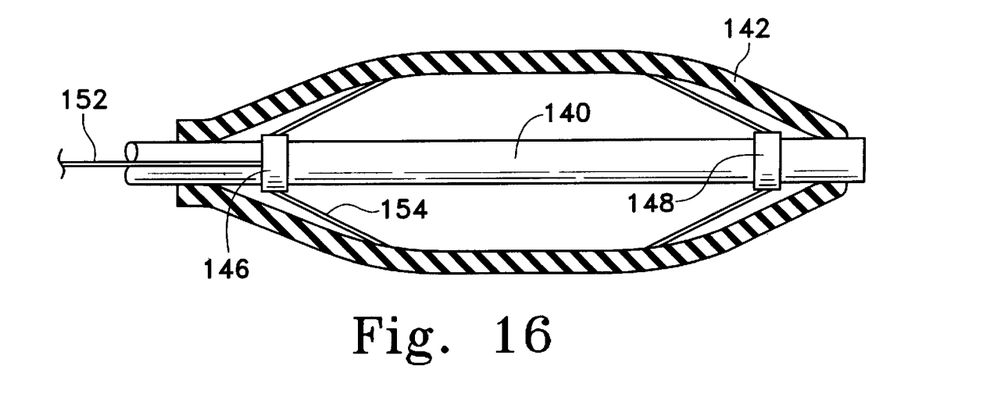
FIG. 16 shows another embodiment, similar to that of FIGS. 14 and 15.

FIG. 16 shows the distal region of an alternative device in which the proximal ring is mounted slidably and attached to a wire 152, while the distal ring is fixed to the catheter shaft. In this embodiment, strands 154 are biased to assume a radially expanded state. Wire 152 is pulled to increase the distance between rings, overcoming the bias to collapse the cage.

Figure 17:
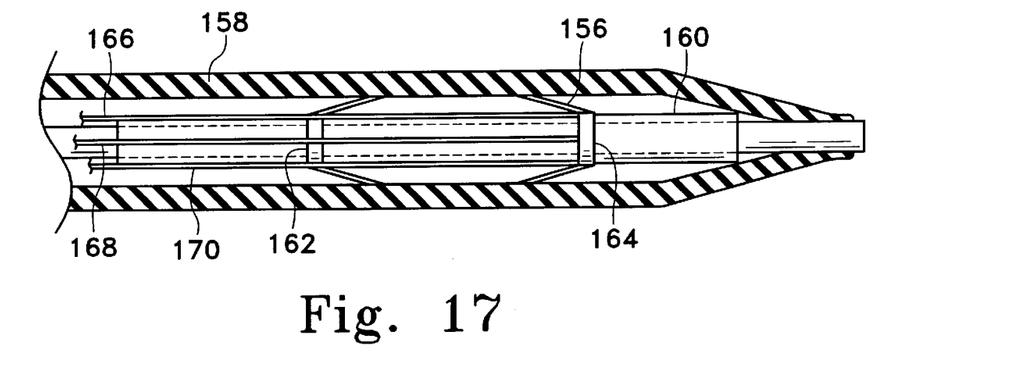
FIGS. 17 and 18 illustrate another embodiment, employing several wires.
Figure 18:
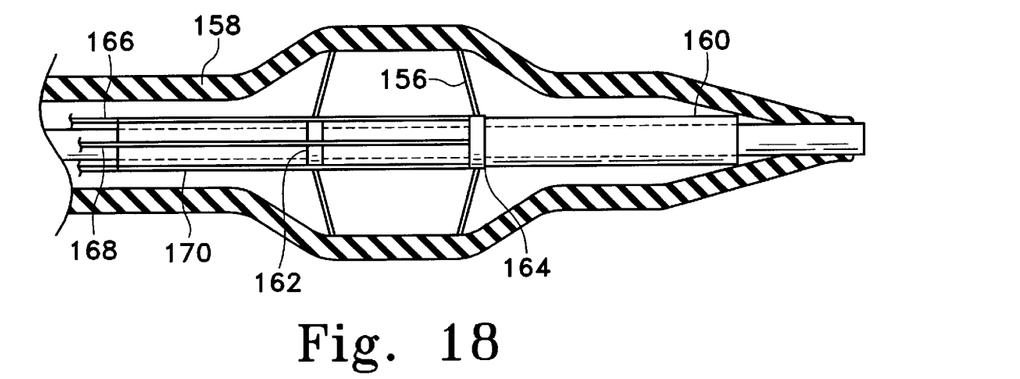

FIGS. 17 and 18 show the distal region of a further embodiment in which strands 156 are coupled to a surrounding tubular expandable wall 158 and a catheter shaft 160. A proximal ring 162 is fixed to the shaft, while a distal ring 164 slides with respect to the shaft. Four wires, three of which are indicated at 166, 168 and 170, are attached to distal ring 164, each associated with a different one of strands 156. The wires can be pulled in unison to expand tubing wall 158 radially as before. Additionally, individual wires can be pulled at different rates, to manipulate the distal end region of catheter shaft 160, primarily for steering.

Figure 19:
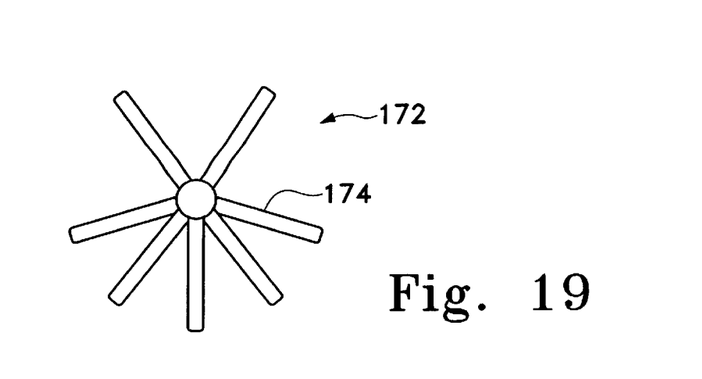
FIG. 19 illustrates an alternative embodiment featuring an unbalanced expansion framework.

FIG. 19 illustrates in distal end view an unbalanced cage 172, i.e. a cage designed to apply uneven radial expansion pressure at different circumferential locations. Each of strands 174 is of the same length and profile. As a result, more expansion pressure is exerted where there is less angular or circumferential spacing between adjacent strands. Alternatively, strands can remain uniformly angularly spaced apart, with strands on one side of the cage configured to exert less force, e.g. through reduced thickness or use of a material with a lower modulus of elasticity.

Figure 20:
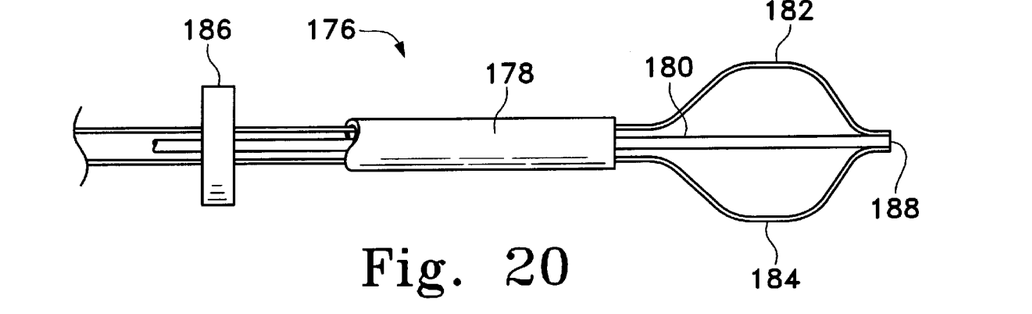
FIG. 20 illustrates an alternative embodiment featuring adjustably mounted strands.

FIG. 20 illustrates a further alternative device 176 including a catheter 178, a stylet 180 movable axially within the catheter and a cage 182 formed of a plurality of strands 184. The strands are integrally fixed by their distal ends to the distal tip of the stylet. The strands are not coupled to the catheter distal end, but rather extend through the catheter to a push/pull device 186 near the proximal end of the catheter. As before, stylet 180 is retractable proximally to radially expand the cage. Strands 184 are adjustably mounted to push/pull device 186. Accordingly, strands 184 can be adjusted to have a uniform length between a stylet distal tip 188 and catheter 178, or alternatively to provide strands with different lengths between these two points. The uniform length is preferred for deployment and positioning of a stent or graft surrounding the catheter distal tip and the radially collapsed cage. During expansion of the stent or graft, axially adjusting the strands within push/pull device 186 provides the option of shortening certain strands relative to the others, to provide an intentionally uneven application of radial expansion force.

Device 176 illustrates one aspect of a salient feature of employing a cage or framework for radial expansions in lieu of an inflatable balloon. The strands of a cage act in concert responsive to manipulation of the stylet or other control device. At the same time, each of the strands is isolated from the other strands, in the sense that its response to stylet movement typically is not influenced by the responses of the other strands. This characteristic permits a wide variety of cage configurations in which different strands representing different radially outward directions can exert different radial expansion forces, expand radially by different distances, or both, in response to a given degree of stylet movement.

Figure 21:
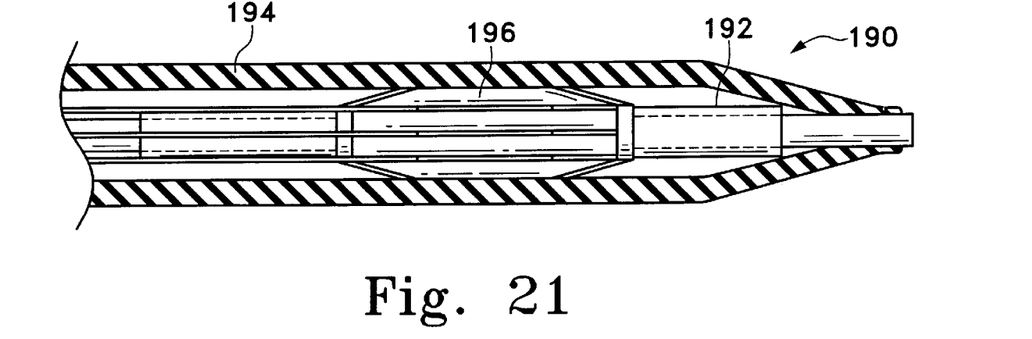
FIGS. 21 and 22 illustrate the employment of drug delivery balloons within the expansion framework.
Figure 22:
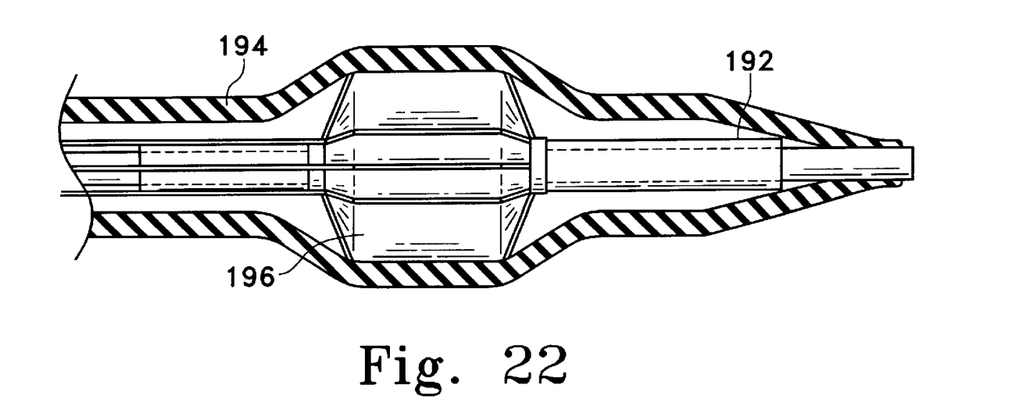

FIGS. 21 and 22 show the distal end region of another alternative embodiment device 190 with a catheter shaft 192 surrounded by an expandable tubing wall 194. Device 190 is similar to the device shown in FIGS. 14 and 15, with the addition of an inflatable bladder 196 formed by a plurality of balloons attached to the strands. One balloon can be attached to each of the strands, with a strand in each case having a lumen in fluid communication with the interior of its associated balloon, for balloon inflation.

Further in connection with these figures, an alternative embodiment can employ an inflatable member similar to bladder 196 (or a single dilatation balloon) in lieu of the cage, i.e. with an expandable sleeve or wall similar to wall 194 surrounding and in direct contact with the bladder or balloon. Even in the absence of the cage, the expandable tubing wall provides several of the same advantages afforded when a cage is present. One of these is burst protection. Should the bladder or balloon burst, it remains contained within the expandable tubing wall. Secondly, the expandable tubing wall due to its residual elastic force tends to assist evacuation of the balloon or bladder, and more effectively contains an evacuated balloon or bladder in a small diameter configuration, avoiding a "winging" problem.

Figure 23:
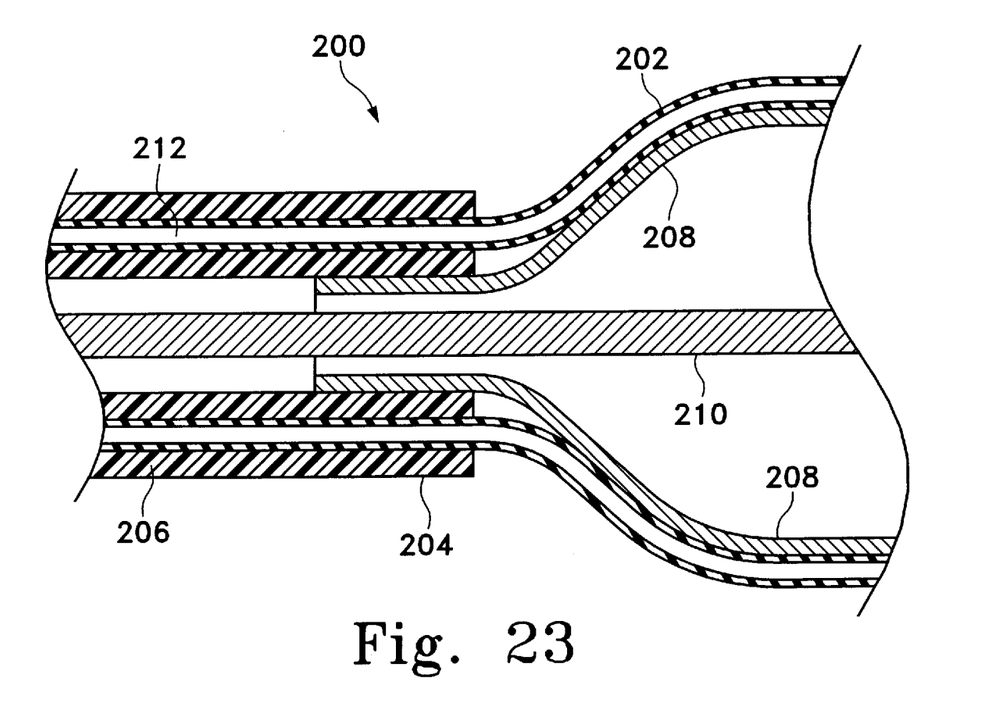
FIGS. 23 and 24 illustrate supplying of drugs using a set of exterior bladders.
Figure 24:
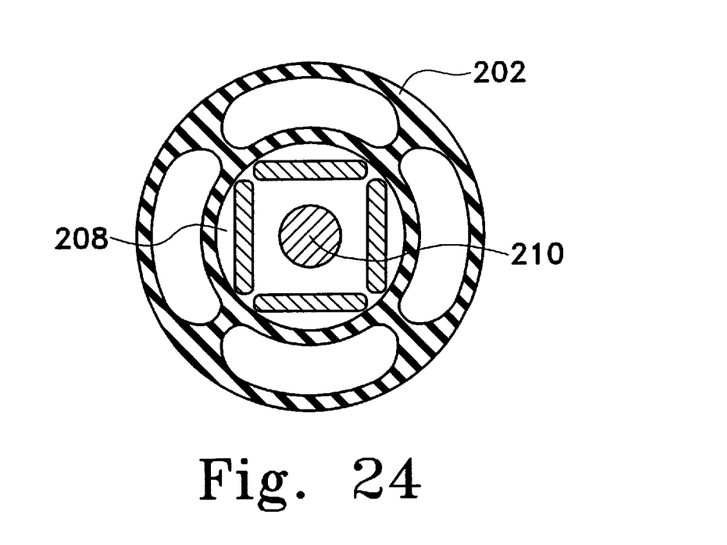

FIGS. 23 and 24 illustrate in part yet another embodiment of device 200, incorporating bladders 202 coupled to a distal end 204 of a delivery catheter 206, in surrounding relation to a plurality of strands 208 mounted to the catheter in an array about a stylet 210. As in other embodiments, the distal end of the strands are coupled to the distal tip of the stylet. Bladders 202 can be porous, to permit the administration of a contrast fluid or drug to the vessel wall during expansion of a stent. This delivery system enables continuous perfusion of blood through the vessel while also profusing drug solutions through the bladders, which may be required for prolonged durations of catheter deployment. The bladders are fluid coupled to drug delivery lumens 212 formed in the catheter. The delivery lumens terminate at Luer lock connectors or other connectors to which a syringe or other infusion mechanism can be connected to inject a drug solution. Bonds between the bladders and lumens may be thermal, mechanical, adhesive or a combination of these. The pores are sufficiently large to permit diffusion of the drug, yet sufficiently small to prevent a backflow of blood.

Thus in accordance with the present invention, grafts and stents can be deployed and expanded by a cage or framework, eliminating a need for a balloon and allowing full profusion during radial expansion. The delivery and deployment system can maintain a graft or stent in a collapsed state during introduction through sheaths positioned by a Seldinger technique or a surgical cut-down. A low profile of the stent or graft is maintained for advancing through vasculature into the target vessel. The system does not perforate the vessel wall when positioning the graft or stent, but rather flexibly follows a guidewire in the target vessel. The device facilitates accurate deployment of the graft or stent, creating intimate contact between the graft or stent and the vessel wall at the target location.

What is claimed is:

1. An apparatus for deploying radially expandable prostheses within body lumens, comprising:

an elongate and flexible catheter having a proximal end and a distal end, said catheter capable of insertion in a body so to position said distal end within a body lumen with said proximal end remaining outside of the body, said catheter disposed at least partially inside a radially expandable prosthesis;

an elongate and pliable stylet disposed at least partially in a lumen of said catheter;

an expansion framework comprising a plurality of elongate compliant strands fixed to said catheter at a first coupling location and fixed to said stylet at a second coupling location, said elongate compliant strands cooperating to define a profile of said framework; and wherein said stylet is movable axially relative to the catheter, and operable from said proximal end of said catheter to alternatively: (i) increase an axial distance between the first and second coupling locations to radially reduce said framework toward a reduced-radius state for intravascularly delivering said prosthesis in an unexpanded state in surrounding relation to said framework, and (ii) reduce the axial distance to radially expand said framework and thereby exert a radial expansion force to radially expand the prosthesis surrounding said framework; and wherein said elongate compliant strands, in a radially expanded state, define a profile of said framework which contacts the prosthesis to radially expand the prosthesis.

2. The apparatus of claim 1 wherein:

the strands are substantially equal in length between the first and second locations, and substantially uniformly arranged about an axis of the catheter.

3. The apparatus of claim 2 wherein:

the strands are substantially parallel to one another and extend axially when in the reduced-radius state, and are curved and circumferentially spaced apart from one another when in the enlarged-radius state.

4. The apparatus of claim 1 wherein the first coupling location is proximal of the second coupling location.

5. The apparatus of claim 1 wherein:

the strands are resilient, and tapered such that the force due to bending varies over the length of each strand.

6. The apparatus of claim 1 further including:

a resilient elastomeric sleeve surrounding the strands and biasing the strands toward the reduced-radius state.

7. The apparatus of claim 6 wherein:

each of the strands, at least along a medial region, is embedded into the elastomeric sleeve.

8. The apparatus of claim 7 further including:

a means for generating an electrical current in the strands, to heat the framework and adjacent tissue at least to a selected temperature above normal body temperature, wherein the strands are electrically conductive.

9. The apparatus of claim 8 wherein:

the means for generating electrical current in the strands includes a power supply, and first and second electrical conductors coupled to the strands at the first and second coupling locations, respectively.

10. The apparatus of claim 8 wherein:

the means for generating electrical current in the strands includes an RF power source, first and second conductors connected to the RF power source, an indifferent electrode spaced apart from the framework, means for electrically coupling the first conductor to the strands, and means for electrically coupling the second conductor to the indifferent electrode.

11. The apparatus or claim 8 further including:

a temperature sensing means disposed proximate the cage/framework.

12. A process for deploying a radially expandable prosthesis, comprising:

positioning an elongate and flexible catheter at a target location within a lumen of a body such that a proximal end of said catheter remains outside the body, said catheter disposed at least partially inside a radially expandable prosthesis, an elongate and pliable stylet disposed at least partially in a lumen of said catheter, and an expansion framework comprising a plurality of elongate compliant strands axially fixed to said catheter at a first coupling location and fixed to said stylet at a second coupling location, said elongate compliant strands cooperating to define a profile of said framework, moving said stylet axially relative to the catheter to reduce an axial distance between the first and second locations to radially expand said framework such that the prosthesis radially expands into contact with said body lumen, reversibly moving said stylet axially relative to the catheter to increase said axial distance and radially reduce said framework such that said prosthesis remains in contact with said body lumen, and proximally withdrawing said catheter from said body lumen, leaving said prosthesis in said body lumen.

13. The apparatus of claim 1, further comprising a pair of handle sections, at least one of said handle sections connected to said styler, wherein relative rotation of said handle sections with respect to one another moves said styler axially with respect to said catheter.

14. The apparatus of claim 13, wherein said handle sections are pivotally interconnected.

15. The apparatus of claim 1, further comprising a rotatable handle connected to said styler and threadably engaged at said proximal end of said catheter, wherein rotation of said handle with respect to said catheter moves said styler axially with respect to said catheter.

16. The apparatus of claim 1, wherein each of said strands comprises a single strand or filament.

17. The apparatus of claim 1, wherein each of said strands comprises a cable made up of a set of small wires or filaments.

18. The apparatus of claim 1, wherein each of said strands comprises a tubular strand.

19. The apparatus of claim 1, wherein said strands are resilient and preformed with a bias toward the radially expanded state.

20. The apparatus of claim 1, wherein said strands are biased toward the reduced-radius state.

* * * * *